(12) United States Patent
Shiomi et al.

(10) Patent No.: US 7,678,047 B2
(45) Date of Patent: Mar. 16, 2010

(54) CHAOLOGIC BRAIN FUNCTION DIAGNOSIS APPARATUS

(75) Inventors: Kakuichi Shiomi, 401, Metro Building, 5-11, Higashi-shimbashi 2-chome, Minato-ku, Tokyo 105-0021 (JP); Naritomo Meguro, Tokyo (JP); Hideyuki Tanaka, Tokyo (JP)

(73) Assignees: Electronic Navigation Research Institute, Tokyo (JP); Kakuichi Shiomi, Tokyo (JP); Mitsubishi Space Software Co., Ltd., Tokyo (JP)

( * ) Notice: Subject to any disclaimer, the term of this patent is extended or adjusted under 35 U.S.C. 154(b) by 1461 days.

(21) Appl. No.: 10/494,920

(22) PCT Filed: Nov. 12, 2002

(86) PCT No.: PCT/JP02/11764

§ 371 (c)(1),
(2), (4) Date: Oct. 14, 2004

(87) PCT Pub. No.: WO03/041589

PCT Pub. Date: May 22, 2003

(65) Prior Publication Data

US 2005/0065412 A1      Mar. 24, 2005

(30) Foreign Application Priority Data

Nov. 13, 2001      (JP)      ............................. 2001-348108

(51) Int. Cl.
A61B 5/00      (2006.01)

(52) U.S. Cl. ......................... 600/300; 600/587; 600/485
(58) Field of Classification Search ....................... None
See application file for complete search history.

(56) References Cited

U.S. PATENT DOCUMENTS

| 5,890,142 | A | * | 3/1999 | Tanimura et al. | ............... | 706/12 |
| 6,483,484 | B1 | * | 11/2002 | Yamazaki et al. | ............... | 345/8 |
| 2004/0243401 | A1 | | 12/2004 | Shiomi et al. | | |

FOREIGN PATENT DOCUMENTS

JP      4-208136      7/1992

(Continued)

OTHER PUBLICATIONS

Translation japanese publication 2000-113347.*

(Continued)

*Primary Examiner*—Robert L Nasser
(74) *Attorney, Agent, or Firm*—Wenderoth, Lind & Ponack, L.L.P.

(57) ABSTRACT

In an apparatus for diagnosing a brain function of a subject 20 by giving a load to a functional site of a living organism of the subject 20, receiving reactions emitted from the living organism of the subject 20 as an electric signal 40, 50, 60 or 70 and analyzing the electric signal 40, 50, 60 or 70, the electric signals 40, 50, 60 and 70 are a voice signal 40, an nystagmus signal 50, a pulse wave signal 60 and a gravity center swinging signal 70. The apparatus selects at least two from among them, calculates chaos theoretical indexes such as Lyapunov exponents according to a chaos theoretical technique, detects changes in the chaos theoretical indexes with passage of time, and collectively evaluates and diagnoses the brain function.

14 Claims, 3 Drawing Sheets

FOREIGN PATENT DOCUMENTS

| | | |
|---|---|---|
| JP | 6-9546 B2 | 2/1994 |
| JP | 6-154167 | 6/1994 |
| JP | 8-586 | 1/1996 |
| JP | 10-52403 | 2/1998 |
| JP | 2000-113347 | 4/2000 |
| JP | 2000-166877 | 6/2000 |
| JP | 2001-129044 | 5/2001 |
| JP | 2001-299702 | 10/2001 |
| JP | 2001-299766 | 10/2001 |

OTHER PUBLICATIONS

Supplementary European Search Report issued Dec. 16, 2008 in the Application No. *EP 02 78 0070*.

A. Minassian et al., "Non Linear Dynamical Analysis of Eye Tracking, Pupil Dilation, and Thought Disturbance", Biological Psychiatry, Elsevier Science, New York, NY, US, vol. 41, No. 7, Apr. 1, 1997, p. 87S, Abstract 297.

Atsuo Murata et al., "Chaotic Analysis of Body Sway", Engineering in Medicine and Biology Society, 1998, Proceedings of the 20th Annual International Conference of the IEEE Hong Kong, China, Oct. 29-Nov. 1, 1998, Piscataway, NJ, USA, IEEE, US, vol. 3, Oct. 29, 1998, pp. 1557-1560.

Toshifumi Sugiura et al., "Chaotic Approach to the Quantitative Analysis of Parkinson's Disease", Engineering in Medicine and Biology Society, 1998, Proceedings of the 20th Annual International Conference of the IEEE Hong Kong, China Oct. 29-Nov. 1, 1998, Piscataway, NJ, USA, IEEE, US, vol. 3, Oct. 29, 1998, pp. 1583-1586.

Hiroshi Yoshimatsu et al., "Fractal Dimension Analysis of Horizontal Binocular Miniature Eye Movement Drift Components", Journal of the Institute of Television Engineers of Japan, vol. 49, No. 8, Aug. 1995, pp. 72-81 (along with English Abstract).

Lucy Yardley et al., "Effect of articulatory and mental tasks on postural control", NeuroReport, Feb. 5, 1999, vol. 10, No. 2, Feb. 5, 1999, pp. 215-219.

Richard Camicioli et al., "Talking while walking: The effect of a dual task in aging and Alzheimer's disease", Neurology, vol. 48, No. 4, 1997, pp. 955-958.

\* cited by examiner

CHAOLOGIC BRAIN FUNCTION DIAGNOSIS APPARATUS

TECHNICAL FIELD

The present invention relates to an apparatus for analyzing a time series signal, such as a voice, a pulse wave, swinging of gravity center, or nystagmus (ocular movement), emitted by a person, and thereby making a diagnosis to determine whether a disease is present in the brain of the person, and judge the progress situation and the state of the disease. The present invention belongs to the field of the medical diagnosis technique.

BACKGROUND ART

In the conventional brain diagnosis, X-ray imaging and brain wave measurement have been conducted as inspections that can be executed with relative ease.

From the 1980's on, a diagnosis for obtaining detailed information in an apparatus of a larger scale, using a positron emission tomography (PET) apparatus or a single photon emission CT (SPECT) apparatus capable of measuring and imaging the dynamics of a cerebral blood flow tracer administered in the brain or the metabolism of glucose in the brain with a gamma camera or a dedicated scanner has also spread, although the diagnosis needs a considerably large-scale apparatus.

As another method, there is also an optical topography apparatus for irradiating the head with a weak infrared light under the present conditions, and measuring the reflection intensity to measure and image the activity state of the cerebral cortex located inside of the skull, and thereby measure the activity situation in the brain.

In the case where an easy method, such as X-ray imaging or brain wave measurement, is used in the conventional brain diagnosis, it is possible to observe a lesion such as cerebral infarction or a tumor, or observe a serious state of a disease, such as the Alzheimer's disease, the Parkinson's disease or the new variant Creutzfeldt-Jakob disease commonly called bovine spongiform encephalopathy (mad cow disease). In this case, however, it is not possible to observe such a progressive disease in its initial state before subjective symptoms occur. When symptoms have appeared, medical measures are already impossible or extremely difficult in many cases. As for some of the above-described diseases, medical techniques for preventing the progress already exist. Nonetheless, it is seldom that such a disease is found in a situation of such a degree as not to interfere with a patient's daily life. In the existing circumstances, therefore, eventually the patient must continue to have a serious disturbance throughout their life.

If the PET, SPECT, optical topography apparatus, or the like is used, the above-described disease can be found before revelation of the symptoms of which the patient is conscious. However, these apparatuses are extremely large-scaled and expensive, and consequently they cannot be introduced into a medical examination such as a complete medical checkup as general inspection.

Nowadays, in situations where brain diseases such as the mad cow disease pose problems, it has been recognized that early finding of a disease occurring in the brain is extremely important to the welfare of mankind. Implementation of a technique and an apparatus for finding the initial state of the above-described diseases, which cannot be found by using a simple method such as X-ray imaging or brain wave measurement, without requiring a complicated large-scale apparatus such as the PET, SPECT, or the optical topography apparatus is wanted keenly.

The present invention has been achieved in order to solve the above-described problems. An object of the present invention is to provide an apparatus that evaluates and diagnoses the initial state and the progress state of a brain disease relatively easily and without applying unreasonable load on a human body.

DISCLOSURE OF THE INVENTION

The present inventors made a study eagerly in order to achieve the object and achieved the following inventions.

In accordance with a first aspect of the invention, there is provided an apparatus for diagnosing a brain function of a subject by giving a load to a functional site of a living organism of the subject, receiving a reaction emitted from the living organism of the subject as an electric signal, and analyzing the electric signal, the apparatus including selecting at least two from among a voice signal, a nystagmus signal, a pulse wave signal and a gravity center swinging signal as the electric signal, calculating chaos theoretical indexes such as Lyapunov exponents according to a chaos theoretical technique, detecting changes in the chaos theoretical indexes with passage of time, and collectively evaluating and diagnosing the brain function.

In accordance with a second aspect of the invention, in addition to the configuration according to the first aspect, the apparatus includes: voice signal processing means for dividing the voice signal, which is input from a voice measuring instrument to the chaos theoretical brain function diagnosis apparatus and converted to a digital signal, into processing units, removing data other than speaking voice data of a human being, and extracting voice data of a single person, when the voice signal is voice data of a plurality of persons; chaos theoretical index calculation means for analyzing speaking voice data of the single person, which is extracted in the voice signal processing means, by using a chaos theoretical technique, calculating a chaos theoretical index, and storing a result of the calculation of the chaos theoretical index in an evaluation and diagnosis database; and chaos theoretical index change state detection means for detecting a change state of the chaos theoretical index by comparing the calculation result of the chaos theoretical index with a chaos theoretical index of the voice signal of the same person at a different time point previously stored in the evaluation and diagnosis database.

In accordance with a third aspect of the invention, in addition to the configuration according to the first aspect, the apparatus includes: nystagmus signal processing means for dividing the nystagmus signal, which is input from a nystagmus measuring instrument to the chaos theoretical brain function diagnosis apparatus and converted to a digital signal, into processing units, and removing data other than nystagmus data; chaos theoretical index calculation means for analyzing nystagmus data with data other than the vibration data removed in the nystagmus signal processing means, by using a chaos theoretical technique, calculating a chaos theoretical index, and storing a result of the calculation of the chaos theoretical index in an evaluation and diagnosis database; and chaos theoretical index change state detection means for detecting a change state of the chaos theoretical index by comparing the calculation result of the chaos theoretical index with a chaos theoretical index of the nystagmus signal of the same person at a different time point previously stored in the evaluation and diagnosis database.

In accordance with a fourth aspect of the invention, in addition to the configuration according to the first aspect, the apparatus includes: pulse wave signal processing means for dividing the pulse wave signal, which is input from a pulse wave measuring instrument to the chaos theoretical brain function diagnosis apparatus and converted to a digital signal, into processing units, and removing data other than pulse wave data; chaos theoretical index calculation means for analyzing pulse wave data with data other than the pulse wave data removed in the pulse wave signal processing means, by using a chaos theoretical technique, calculating a chaos theoretical index, and storing a result of the calculation of the chaos theoretical index in an evaluation and diagnosis database; and chaos theoretical index change state detection means for detecting a change state of the chaos theoretical index by comparing the calculation result of the chaos theoretical index with a chaos theoretical index of the pulse wave signal of the same person at a different time point previously stored in the evaluation and diagnosis database.

In accordance with a fifth aspect of the invention, in addition to the configuration according to the first aspect, the apparatus includes: gravity center swinging signal processing means for dividing the gravity center swinging signal, which is input from a swinging measuring instrument to the chaos theoretical brain function diagnosis apparatus and converted to a digital signal, into processing units, and removing data other than gravity center swinging data; chaos theoretical index calculation means for analyzing gravity center swinging data with data other than the gravity center swinging data removed in the gravity center swinging signal processing means, by using a chaos theoretical technique, calculating a chaos theoretical index, and storing a result of the calculation of the chaos theoretical index in an evaluation and diagnosis database; and chaos theoretical index change state detection means for detecting a change state of the chaos theoretical index by comparing the calculation result of the chaos theoretical index with a chaos theoretical index of the gravity center swinging signal of the same person at a different time point previously stored in the evaluation and diagnosis database.

According to the first to fifth aspects of the invention, the living organism signals, such as the speaking voice, pulse wave, gravity center swinging and nystagmus, converted to digital data according to the chaos theoretical technique are analyzed and the chaos theoretical indexes are calculated. Thereby, the activity state of the brain is sensed from the state of the chaos theoretical indexes. Therefore, examination data concerning the health state of the brain can be obtained from body signals that can be easily sampled. Therefore, the present invention can be used in a preliminary diagnosis preceding precision examination, which needs a large-scale device and a complicated diagnosis technique, and a medical examination in a medical checkup or the like.

Furthermore, in accordance with the first aspect of the invention, at least two signals can be selected from among the living organism signals corresponding to the second to fifth aspects, and the brain function can be evaluated and diagnosed with a precision higher than that of the conventional technique, by using collectively chaos theoretical indexes of them.

In accordance with a sixth aspect of the invention, in addition to the configuration according to any one of the first to fifth aspects, the chaos theoretical brain function diagnosis apparatus includes a load generation section and a sensor section, the load generation section includes at least one of an image display device for imposing a visual load on the subject, a speaker for imposing an auditory load on the subject, and a sporting good having a function of swinging the gravity center, and the sensor section includes at least two measuring instruments of a microphone, a voice measuring instrument, a nystagmus instrument, a nystagmus measuring instrument, a pulse wave sensor, a pulse wave measuring instrument, a gravity center swinging instrument, and a swinging measuring instrument.

According to this, in addition to the effects according to any one of the first to sixth aspects, an evaluation and a diagnosis of the brain function are conducted by comparing data in a brain function evaluation and diagnosis database, which stores data for conducting an evaluation and a diagnosis of the brain function, with calculation results of the chaos theoretical indexes. As a result, an evaluation and a diagnosis with high precision based on basic data for evaluation and diagnosis can be performed.

In accordance with an eighth aspect of the invention, in addition to the configuration according to any one of the first to seventh aspects, the chaos theoretical brain function diagnosis apparatus includes measuring instrument load control means for controlling a load state generated by the load generation section, and at least one of display contents displayed on an image display device, sound contents generated by the speaker, and motion contents generated in the sporting good is adjusted on the basis of at least one of a chaos theoretical index value of speaking voice data, a chaos theoretical index value of nystagmus data, a chaos theoretical index value of pulse wave data, and a chaos theoretical index value of gravity center swinging data, which are found by the chaos theoretical index calculation means.

Here, in the chaos theoretical analysis, it is sufficient if a signal such as the speaking voice can be sampled as one-dimensional time series data. Also in the case where a plurality of data obtained by simultaneously sampling the same subject are used, it is possible in principle to process the data individually, finally combine respective evaluation results, and obtain an evaluation result as a whole.

In the apparatus according to the present invention, a variation of a living organism signal generated by imposing a load on the subject is also grasped as an expression of a chaotic behavior of the living organism, and processed by using the chaos theoretical technique. As a result, a more synthetic brain function diagnosis with a higher sensitivity is implemented.

According to the eighth aspect of the invention, the chaos theoretical brain function diagnosis apparatus includes measuring instrument load control means for controlling a load state generated by the load generation section, and at least one of display contents displayed on an image display device, sound contents generated by the speaker, and motion contents generated in the sporting good is adjusted on the basis of at least one of a chaos theoretical index value of speaking voice data, a chaos theoretical index value of nystagmus data, a chaos theoretical index value of pulse wave data, and a chaos theoretical index value of gravity center swinging data, which are found by the chaos theoretical index calculation means. By imposing a controlled load on the brain as a bias, therefore, accurate measurement can be performed even for a slight brain disease.

BEST MODE FOR CARRYING OUT THE INVENTION

Hereafter, the present invention will be described on the basis of an embodiment.

Figure 1:
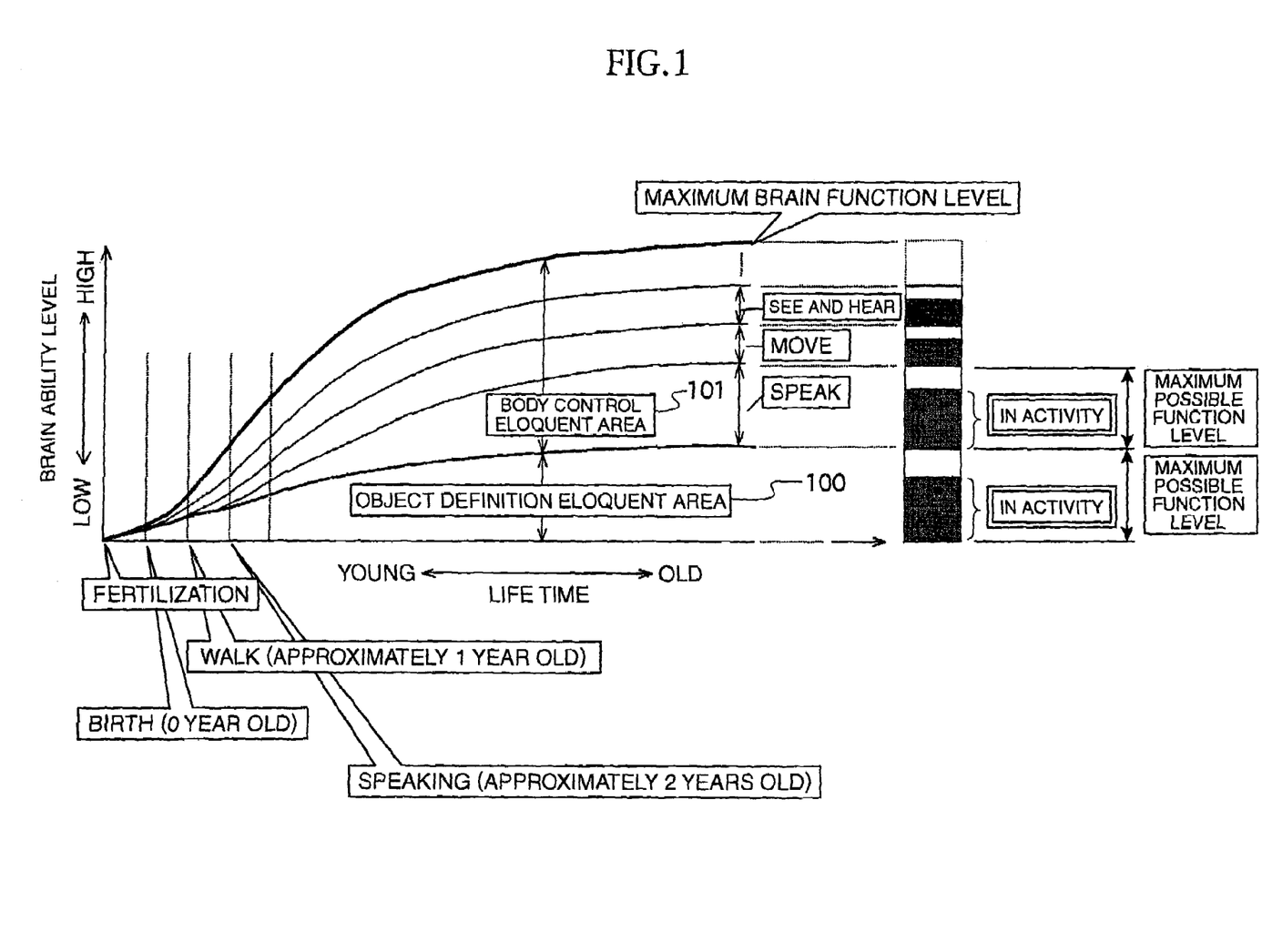
FIG. 1 is a graph showing changes of brain ability levels in the object definition eloquent area and a body control eloquent area with age according to an embodiment of the present invention.

FIG. 1 is a graph showing changes of brain ability levels in the object definition eloquent area 100 and a body control eloquent area 101 with age according to an embodiment of the present invention.

The present inventors have considered that in order for a human being to take significant action it is necessary to describe contents of the action by using language of the human being. Therefore, the present inventors have decided to grasp the brain function as a combination of a function of describing an object of a motion of a body inclusive of speaking and a function of controlling speaking or the body motion according to the described object.

By the way, the function of describing the object of the body motion inclusive of speaking in the above described brain function includes a function of managing storage that functions as a dictionary for describing the object.

Object information in which certain one object corresponds to contents described by the function of describing the object of the brain (hereafter referred to as "object definition function." In the case where a site for implementing this function is handled as physical existence, this function is referred to as object definition eloquent area 100) is sent to a function of controlling a plurality of motions required implementing the described contents (hereafter referred to as "body control function."

In the case where a site for implementing this function is handled as physical existence, this function is referred to as body control eloquent area 101), as a signal including the object information. In the function of controlling individual motions, a signal for controlling a muscle to be controlled is generated from the object information, and sent to a body organ to be controlled.

Receptor organs forming five sensory organs feed back information for generating objects to the object definition eloquent area 100 by seeing or hearing an object subject.

Information acquired by a receptor organ such as eyes or ears is stored and managed in the object definition eloquent area 100.

In the brain, both the object definition eloquent area 100 and the body control eloquent area 101 obtain energy for maintaining the functions by metabolizing glucose. If metabolic waste matters generated by the metabolism increase, the brain lowers its function level in order to avoid damage in the brain itself.

For recovering from the lowered function level, rest of the brain is necessary. If the metabolic waste matters are removed during this rest, activity at a high function level in the brain becomes possible again.

The fall in the function level of the brain also occurs in the case where the capacity of the brain itself is decreased by physical or chemical damage. The fall in the function level of the brain also occurs in the case where a disturbance has occurred in internal secretion such as hormone required to maintain the brain function.

In the case where the fall in the function level of the brain is caused by physical or chemical damage or the like, recovery of the function level is considered to be almost impossible as of today. In the case where the fall in the function level of the brain is caused by disturbance in endocrine, it is possible to recover the brain function level by eliminating or compensating the disturbance in endocrine with medical treatment, unless the brain is subjected to physical or chemical damage.

However, it is considered that the brain does not have a structure in which eloquent areas taking charge of respective functions are separated definitely, but the eloquent areas are highly redundant and complementary. In the case where, even if physical or chemical damage is caused, the damage is slight, or in the case where, even if the physical range of damage extends over the whole brain, the relative weight ratio or capacity ratio of the brain is small, it is not seldom that the disturbance is not actualized in the daily life because there is singularly large redundancy in the brain as compared with other body organs.

If some disease occurs in such a brain and the disease occurs in a part of the brain, a symptom corresponding to the site appears as the disease progresses. For example, for dopamine secretion disturbance such as the Parkinson's disease, the activity is lowered in the whole brain by deficiency of dopamine.

In situations where the whole brain is soiled with abnormal protein as in the Alzheimer's disease or the mad cow disease, disturbances occur because the activity of the whole brain is lowered by its progress in the same way, or a discrepancy occurs in information exchange between functional sites.

No matter whether the brain disease is local or general, an extreme fall of the activity in the brain or a significant miscarriage in cooperation between functional sites in the brain appears as function disturbance in both mind and body.

In situations where function disturbance appearing in mind or body is been conscious of, or observed by another person in the daily life, the disease has already progressed in such a state that it cannot be compensated by the reliability the brain has. In brain disturbances, it is in most cases extremely exceptional to re-acquire the function once lost. Therefore, recovery from the actualized disturbance is not achieved throughout the life.

Therefore, it brings about a marked advance in the medical field to establish a brain function diagnosis technique having sensitivity capable of observing and detecting the initial symptom in the progress state before self-consciousness.

In the prior invention (Japanese Patent Application Publication No. 2001-116408 and Japanese Patent Application Publication No. 2001-280105), the present inventors describe that the brain function of a speaker can be measured by analyzing a spoken voice. In addition, however, the present inventors have found that an early diagnosis of a brain disease such as the Alzheimer's disease, the Parkinson's disease or the mad cow disease can be easily implemented by improving the analysis technique and analyzing other living organism signals as hereafter described.

Figure 2:
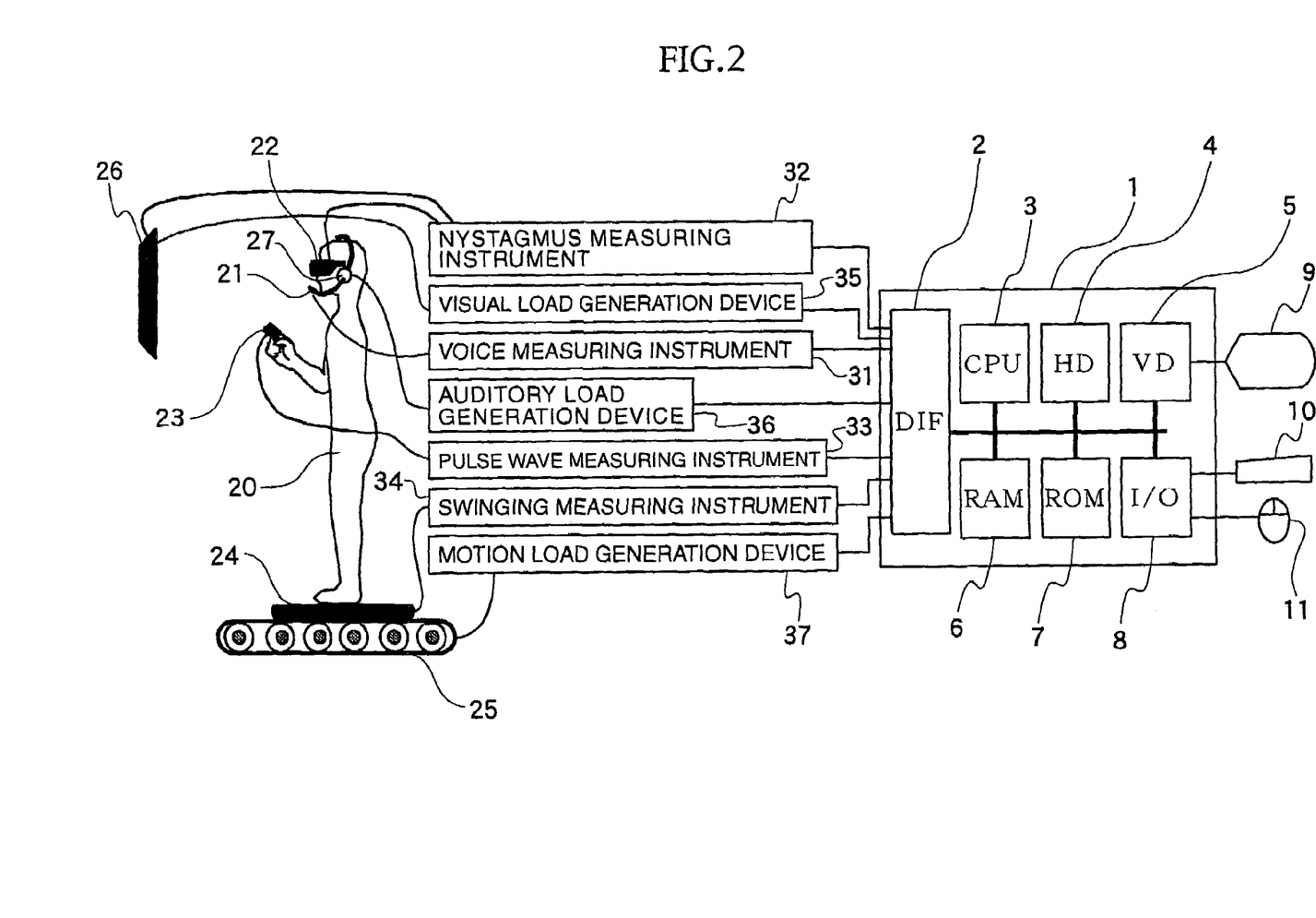
FIG. 2 is a hardware configuration diagram according to the embodiment.
Figure 3:
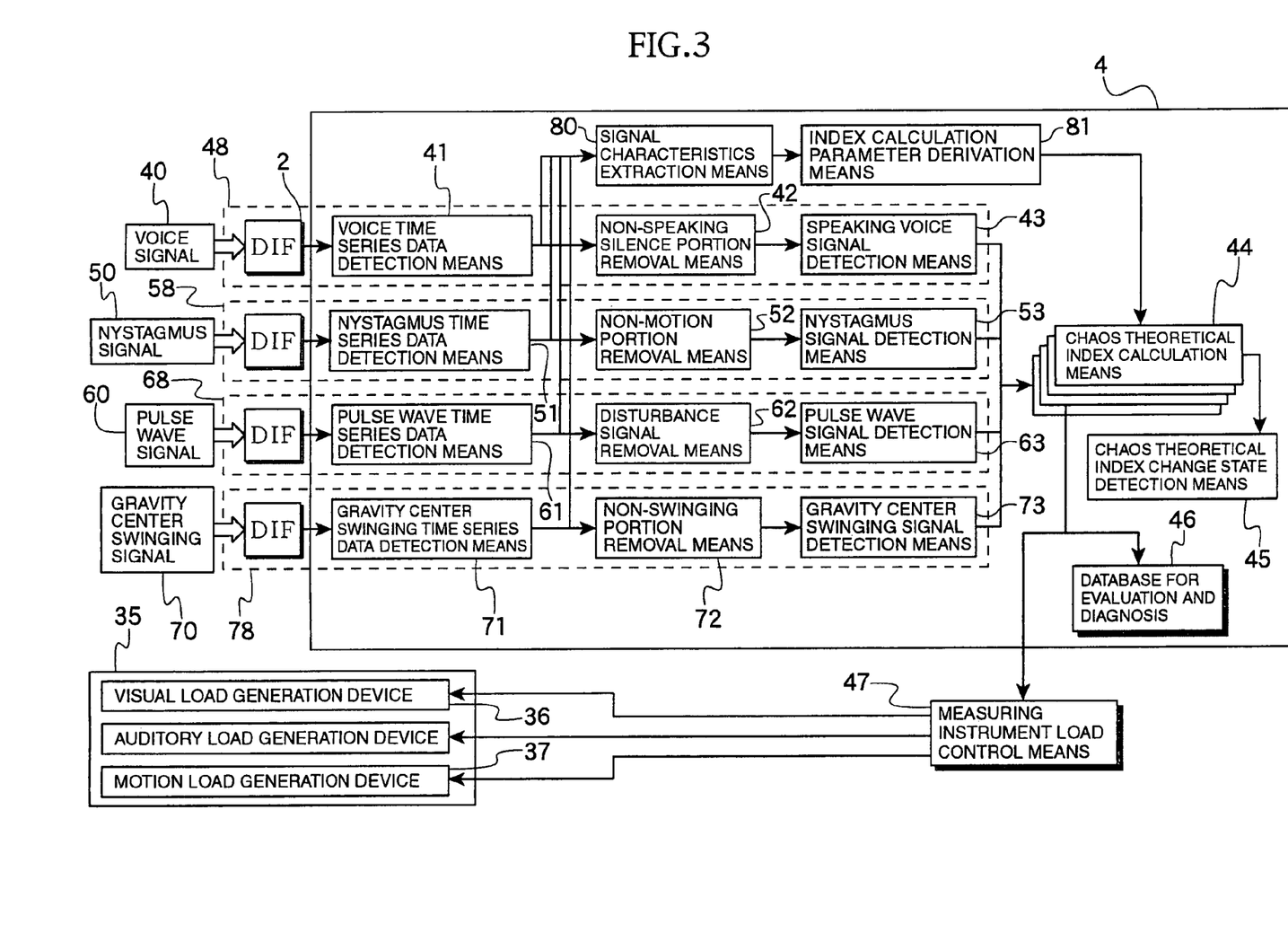
FIG. 3 is a function block diagram showing a brain function diagnosis program in an apparatus according to the present invention mainly recorded in a hard disk device in a computer according to the embodiment.

FIGS. 2 to 3 show block diagrams of an embodiment according to the present invention.

FIG. 2 is a block diagram showing a configuration example in the case where a chaos theoretical brain function diagnosis apparatus according to the present invention (hereafter referred to as "apparatus according to the present invention") is implemented by using a computer.

In FIG. 2, reference numeral 1 denotes a computer. The computer 1 includes a hard disk device 4 on which a diagnosis program (hereafter referred to as "brain function diagnosis program") PG for detecting and quantifying a fall in function level of the object definition eloquent area 100 and the body control eloquent area 101 is recorded. A program code of the brain function diagnosis program PG is stored on the hard disk device 4, and in addition the hard disk device 4 includes an evaluation and diagnosis database 46 described later (see FIG. 3). As a medium for recording the program, a recording medium such as a flexible disk, a CD-ROM or MO, which can be used by various computers, and its drive device may be used.

A chaos analysis program is included in program codes of the brain function diagnosis program PG. This chaos analysis program is a program for calculating chaos theoretical indexes by conducting a chaos analysis on digital data of a voice signal 40, an nystagmus signal 50 representing an eyeball motion, a fingertip pulse wave signal 60 and a gravity center swinging signal 70 indicating the movement of the gravity center, which are read by the brain function diagnosis program PG.

Furthermore, a microphone 21 for inputting a voice of a subject 20, a voice measuring instrument 31 for setting and changing a sampling period and a dynamic range (bit length) in sound volume level adjustment and digital conversion to take this voice in the computer 1, a nystagmus instrument 22 for electrically detecting the vibration and motion of an eyeball of the subject 20, a nystagmus measuring instrument 32 for taking this nystagmus signal in the computer 1, a fingertip pulse wave sensor 23 for measuring the pulse wave at the fingertip of the subject 20, a pulse wave measuring instrument 33 for taking this pulse wave signal into the computer 1, a gravity center swinging instrument 24 for making the subject 20 walk on a walker 25, thereby imposing a motion load on the subject, and measuring the movement of the gravity center, and a swinging measuring instrument 34 for taking the gravity center swinging signal in the computer 1 are connected to the computer 1.

These measuring instruments attached and connected to the subject 20 are used to take signals measured from the subject 20 in the computer 1 in real time.

Furthermore, the computer 1 includes a video output device 5. A display device 9 for displaying control order contents and measurement results in operation of the present invention apparatus is connected to the video output device 5. Furthermore, the computer 1 includes an I/O control device 8. A keyboard 10 and a mouse 11 respectively functioning as keying input means and a pointing device are connected to the I/O control device 8.

Furthermore, an image display device 26 for imposing visual load on the subject 20 is connected to a visual load generation device 35 as a "load generation section." An ear speaker 27 for imposing-auditory load on the subject 20 is connected to an auditory load generation device 36. The walker 25 of belt conveyor type including rollers is connected to a motion load generation device 37. In addition, the visual load generation device 35, the auditory load generation device 36 and the motion load generation device 37 are connected to a data input-output interface 2 to control them by the computer 1. By the way, as the walker 25, a hemispherical or semi-cylindrical sporting good for balance the vibration state of which can be controlled by external control may be used.

A RAM 6 and a ROM 7 are incorporated in the computer 1 around a CPU 3 as storage means for developing respective program codes and implementing functions. The data input-output interface 2 is also incorporated in the computer 1 to conduct interface processing, such as conversion to digital data, which can be processed by the computer 1, in the case where signals measured by the voice measuring instrument 31, the nystagmus measuring instrument 32, the pulse wave measuring instrument 33 and the swinging measuring instrument 34 are analog signals.

In the case where the present invention apparatus is implemented by such a computer 1, the image display device 26, the ear speaker 27, the walker 25, the visual load generation device 35, the auditory load generation device 36 and the motion load generation device 37 form a "load generation section" in the present embodiment. The microphone 21, the nystagmus instrument 22, the fingertip pulse wave sensor 23, the gravity center swinging instrument 24, the voice measuring instrument 31 the nystagmus measuring instrument 32, the pulse wave measuring instrument 33 and the swinging measuring instrument 34 form a "sensor section." The CPU 3 conducts chaos analysis on digital data obtained by the data input-output interface 2 in accordance with the chaos analysis program PG stored in the hard disk device 4. Thus there are chaos theoretical index calculation means 44 for calculating chaos theoretical index, and chaos theoretical index change state detection means 45 for detecting a change state on the basis of a result of the calculation. In addition, the CPU 3 functions also as means for dividing digital data obtained by the data input-output interface 2 into processing units, and functions also as means for removing portions having no signals.

In addition, the hard disk device 4 functions also as means for storing the calculation result of the chaos theoretical index. By the way, it is also possible to use the RAM 6 instead of the hard disk device 4, which is nonvolatile storage means.

In the apparatus according to the present invention having the configuration described above, it is possible without problems for a healthy person to have a daily talk while conducting a walking motion on the belt conveyor walker 25. It is also possible to follow a change in walking speed and to interpret and watch symbols and marks displayed on the image display device 26 installed before eyes. From such a state, a brain function examination procedure is started.

In the examination procedure, the subject 20 is first made to read aloud a composition displayed on the image display device 26 and conduct interpretation of the symbols and marks by speaking. The load level of the brain relating to the speaking is measured, and the walking speed is adjusted. In a state in which a natural walking motion is possible as if the subject 20 strolls, swinging of gravity center of the subject 20 is measured and the load level of the brain relating to the control of the gravity center is measured. Or the load level may be measured by conducting a simple motion formed as a game, such as a whack-a-mole game, or a game aiming at dancing to music.

Subsequently, in the examination procedure in the present invention apparatus, the speed of the walker 25, which is the "load generation section," is adjusted and the load level of the brain relating to the control of the gravity center is increased, while making the subject 20 continue the work relating to the speaking. In this way, the change of the load level of the brain relating to speaking is measured.

By the way, in the measurement of the load level of the brain relating to speaking, the speed of the walker is controlled so as to always keep the load level of the brain relating to the control of the gravity center constant or increase the load level at a constant temporal state in some diagnosis procedures. In this way, control of the speed of the walker corresponding to each of procedures set for various diagnosis purposes is conducted.

By the way, as for the "load generation section" in the apparatus according to the present invention, the combination of devices forming the load generation section can be arbitrarily set. In the case where the diagnosis purpose can be sufficiently achieved by making the subject 20 read aloud newspaper or the like as the load, the device such as the walker 25 for imposing the motion load can be removed from the configuration.

A processing flow of a signal measured by the "sensor section" will now be described on the basis of FIG. 3.

FIG. 3 is a function block diagram mainly showing a brain function diagnosis program PG in an apparatus according to the present invention recorded on the hard disk device 4 in the computer 1.

Signals measured in the "sensor section" are the voice signal 40, the nystagmus signal 50, the fingertip pulse wave signal 60 and the gravity center swinging signal 70. These signals are input to and processed by voice signal processing means 48, nystagmus signal processing means 58, pulse wave signal processing means 68 and gravity center swinging signal processing means 78, respectively. Thereafter, these signals are processed by the chaos theoretical index calculation means 44 and the chaos theoretical index change state detection means 45. The voice signal processing means 48 includes the data input-output interface 2, voice time series data detection means 41, non-speaking silence portion removal means 42 and speaking voice signal detection means 43. The nystagmus signal processing means 58 includes the data input-output interface 2, nystagmus time series data detection means 51, non-motion portion removal means 52 and nystagmus signal detection means 53. The pulse wave signal processing means 68 includes the data input-output interface 2, pulse wave time series data detection means 61, disturbance signal removal means 62 and pulse wave signal detection means 63. The gravity center swinging signal processing means 78 includes the data input-output interface 2, gravity center swinging time series data detection means 71, non-swinging portion removal means 72 and gravity center swinging signal detection means 73.

First, the case where the voice signal 40 is used as the input will now be described.

Voice of the subject 20 is taken in the apparatus according to the present invention by using the microphone 21 or the like. If the voice signal 40 taken in is an analog signal, digital conversion is conducted by the data input-output interface 2 and resultant digital voice data is input to the voice time series data detection means 41 to divide continuous digital voice data into processing units required in subsequent processing.

Subsequently, as preprocessing of analysis using the chaos theoretical technique, processing for removing non-speaking voice sounds other than speaking voices of a human being from the divided voice digital data obtained by the voice time series data detection means 41 is conducted by the non-speaking silence portion removal means 42.

Specifically, the non-speaking voice sound to be removed is a collision attenuation sound, a collision reverberation sound, a double collision sound, a multiple collision sound, a crush sound, a fricative sound, and silence. On the basis of the center frequency, reverberation time and bandwidth of the original sound, feature extraction is conducted and separation and removal of non-speaking voice sound are conducted.

As a result of the above-described processing, the divided voice digital data with non-speaking voice sound removed becomes divided voice digital data with only the speaking voice component of the human being left. In the case where speaking voice signals of a plurality of persons are input, separation into individual speaking voices is conducted in the speaking voice signal detection means 43, because it is necessary to conduct the following analysis using chaos theoretical technique individually.

Specifically, on the basis of center frequencies, reverberation time and bandwidths of all speakers, feature extraction is previously conducted and comparison with voice signals measured in real time is conducted.

In addition, as preprocessing for analysis using the chaos theoretical technique, signal characteristics such as the dynamic range (such as intensity and amplitude), pitch (such as frequency characteristics and time change rate), and an offset quantity are extracted from the voice digital data, which has been obtained by the voice time series data detection means 41, by signal characteristics extraction means 80. In order to obtain predetermined required diagnosis purpose and diagnosis precision, parameters such as data acquisition time and embedded dimension are derived by index calculation parameter derivation means 81.

Subsequently, in the chaos theoretical index calculation means 44, analysis is conducted to calculate the chaos theoretical index according to the chaos theoretical technique by using the voice digital data output by the speaking voice signal detection means 43 and the parameters derived by the index calculation parameter derivation means 81.

Specifically, it is made clear that if a speaking voice of a human being is processed as a time series signal, the fractal dimension of the waveform is experimentally at most six-dimensional. Therefore, it is decided to form strange attractors in at most six-dimensional space, and processing is conducted to generate attractors. As for its calculation processing, calculation processing using the method disclosed in Japanese Patent Application Laid-Open Publication No. 2000-113347, entitled "Fatigue and doze sensing apparatus using voices and recording medium" can also be used.

Thereafter, in order to temporarily hold the chaos theoretical index calculated every moment in a time series and indicate the state change quantitatively, in the chaos theoretical index change state detection means 45, the value of the chaos theoretical index and the change of the chaos theoretical index and its change range are found and the tendency of the time series change is detected. As the method for finding the change tendency, there is a method of finding a characteristic curve by using the running average, least square approximation, Kalman filter or the like. Furthermore, by comparing the chaos theoretical index with a chaos theoretical index of the voice of the same subject 20 at a different time point previously stored in the evaluation and diagnosis database 46 provided in the hard disk device 4, relative comparison with respect to part reference points is conducted.

By the way, in the evaluation and diagnosis database 46, for example, the chaos theoretical indexes measured at the time of periodic medical checkup conducted once a year are accumulated. In the case of a subject 20 who keeps going to a hospital, chaos theoretical indexes continuously measured every week or every day are accumulated in the evaluation and diagnosis database 46. Thus, it becomes possible to observe medium-range and long-range states of the brain function change. It also becomes possible to conduct comparison with an average value by accumulating data of a plurality of subjects 20.

Here, the average activity of the brain can be presumed from a temporal average of the first Lyapunov exponent calculated by processing the speaking voice according to the chaos theoretical technique. It is known that if a state in which the temporal average of the first Lyapunov exponent value is comparatively high continues for at least several tens minutes the subject 20 is conscious of fatigue.

By the way, it is also possible to provide a brain function evaluation and diagnosis database, which previously stores basic data for making a diagnosis in a category of desired disease, in the hard disk device 4 in the present invention apparatus. It is also possible to construct the brain function evaluation and diagnosis database in a remote place by using the Internet or the like. As for data stored in the brain function evaluation and diagnosis database, for example, an average chaos theoretical index in the initial state of a brain disease, a chaos theoretical index in self-consciousness of fatigue, and standard values of blood pressure, pulsation and weight for height are conceivable.

Also in the case where the input data is the nystagmus signal 50, the pulse wave signal 60 or the gravity center swinging signal 70, the processing flow is nearly the same as that in the case of the voice signal 40.

Specifically, the case where the input data is the nystagmus signal 50 will now be described. An eyeball motion is measured by the nystagmus measuring instrument 32, and the nystagmus signal 50 is taken in the apparatus according to the present invention. If the nystagmus measuring instrument 32 has an analog-digital conversion function, the nystagmus signal 50 is taken in as digital data. If the nystagmus measuring instrument 32 has not the analog-digital conversion function, the nystagmus signal 50 is taken in as analog data as it is.

If the nystagmus signal 50 taken in is analog data, it is converted to digital data by the data input-output interface 2. Resultant digitized nystagmus data is divided into processing units required in subsequent processing by the nystagmus time series data detection means 51. Thereafter, data other than the nystagmus data are removed by the non-motion portion removal means 52. The nystagmus data is detected by the nystagmus signal detection means 53. Furthermore, in the same way as the case of voice, signal characteristics are extracted from the divided nystagmus data obtained by the nystagmus time series data detection means 51, by the signal characteristic extraction means 80. Parameters to be used in the chaos theoretical index calculation are derived by the index calculation parameter derivation means 81.

Subsequently, in the chaos theoretical index calculation means 44, analysis is conducted to calculate the chaos theoretical index according to the chaos theoretical technique by using the nystagmus data output by the nystagmus signal detection means 53 and the parameters derived by the index calculation parameter derivation means 81. Subsequent processing is the same as in the case of voice, and consequently duplicated description will be omitted. Processing in the case where the input data is the pulse wave signal 60 or the gravity center swinging signal 70 is also the same as the case of the voice signal 40 or the nystagmus signal 50, and consequently duplicated description will be omitted.

Here if the pulse wave is processed by the chaos theoretical technique, a fall in the brain function caused by a brain disease is observed as a fall in the first Lyapunov exponent and as a change in another chaos theoretical index value such as KS entropy.

Furthermore, if the swinging of the gravity center or the nystagmus is analyzed in the way of the chaos theory, a fall in the first Lyapunov exponent with minute or hour taken as the unit becomes an index for a fall in the brain function level caused by fatigue, and the fall in the first Lyapunov exponent in a time scale with month or year taken as the unit becomes an index for a fall in the brain function caused by a brain disease.

Furthermore, in the typical walking motion of a human being, it is known that the movement of the gravity center draws a locus similar to a sine wave. If the swinging of the gravity center at the time of walking is measured as a time series signal, a chaotic structure caused by superposition of influences of fatigue of the subject on the sine wave is observed.

By selecting two or more from among calculation results of chaos theoretical indexes for voice, nystagmus, pulse wave and gravity center, combining a plurality of calculation results, and collectively evaluating and diagnosing relative changes of chaos theoretical indexes, it is possible to conduct evaluation and diagnosis with a precision higher than the case of a single calculation result. These collective evaluation and diagnosis may be displayed on the display device 9.

In the apparatus according to the present invention, the change of the load level of the brain relating to speaking can be measured by using the brain load relating to the gravity center control, which can be controlled relatively easily by controlling the "load generation section" on the apparatus side, as the bias. Therefore, it becomes possible to find a brain disease, which has been difficult to find until it becomes serious when relying upon only diagnosis using the speaking voice, a long time before the speaking activity is interfered with.

Furthermore, by using devices for generating various brain loads in combination with each other and controlling a load level loaded on the brain as the bias, it is possible to quantitatively diagnose the degree of progress even for a slight disease state, which has been difficult to quantify in the conventional technique because it has been masked by the redundancy the brain has.

In measuring instrument load control means 47 provided outside the hard disk device 4, there is a function of monitoring and controlling the load state generated by the "load generation section." It is possible to adjust the load bias loaded on the brain by adjusting display contents of the image display device 26 connected to the visual load generation device 35 and sound contents generated in the ear speaker 27 connected to the auditory load generation device 36 and adjusting the walker 25 connected to the motion load generation device 37.

As heretofore described, it is considered that the diagnosis of a brain disease becomes possible by continuously measuring the chaos of the living organism. As described earlier, the brain has remarkable redundancy as compared with other body organs. In the case of a diagnosis using only a limited living organism signal, therefore, it is difficult to implement a sufficient sensitivity when the brain disease state is slight, no matter which chaos is diagnosed.

Furthermore, in the case of a diagnosis using only a limited living organism signal, a living organism signal extending over a relatively long time becomes necessary in diagnosis of every time. For example, in the case where only the speaking voice is used, it is necessary to acquire the continuous speaking voice over several tens minutes even when the average brain fatigue is measured, although it also depends upon the fatigue state of the subject 20. Thus, the diagnosis is not easy.

Also in the case where the gravity center swinging or the nystagmus is used, it is necessary to acquire and process data over approximately several tens minutes in the same way. Although they are simple diagnosis techniques as compared with the use of an apparatus such as the PET or SPECT, it is not easy to implement a proper diagnosis for the aged having declined strength or a person fatigued from some reason at the time of the diagnosis.

Furthermore, in the conventional chaos diagnosis using the gravity center swinging, nystagmus and pulse wave, in principle, a desired living organism signal is measured with the subject 20 in a relatively rest state including the case where the subject 20 is sitting calmly or standing naturally.

This aims at preventing the subject 20 from generating unnecessary noise and thereby lowering the diagnosis precision, because a change in living organism signal generated by imposing a load on the subject 20 is grasped as random noise. It is frequently said "a good idea is thought of or a solution to a problem is found not when a person is thinking steadily at a desk, but when the person is strolling or conducting some relatively simple work." In the brain model in the present invention, this is understood to be caused by a fact that the operation work, which increases the load of the body control eloquent area 101, has raised the activity of the object definition eloquent area 100, which provides the body control eloquent area 101 with control information.

The phenomenon expressed as "it is easier to shape up ideas when thinking while speaking than when thinking silently" is also understood in the same way to be caused by a fact that the rise of activity in the object definition eloquent area 100 and the rise of the load level in the body control eloquent area 101 are in sympathy with each other.

In the brain model in the present invention, the object definition eloquent area 100 is a part controlled by a so-called operating system in the computer, and only one is defined in the personal brain. The body control eloquent area 101 is a so-called I/O subsystem in the computer, and a plurality of them can be defined for respective organs, which constitute a body.

In the apparatus according to the present invention, some of a plurality of body control eloquent areas 101, such as a speaking motion field, motion fields for controlling physical motions of respective body organs, and a body control eloquent area 101 relating to the regulation of the visual function, are worked upon by, for example, giving a stimulus from the outside. The object definition eloquent area 100 is compelled to generate information concerning the control of those body control eloquent areas 101. In other words, controlled loads are generated as the biases. As a result, a part of the processing capacity in the object definition eloquent area 100 is consumed compulsorily. It is thus made possible to detect with a higher sensitivity the fall of the brain function concerning the object definition eloquent area 100, which is difficult to be actualized in the conventional single living organism function evaluation.

The previous brain model will be described in a simplified form. It is supposed that the object definition eloquent area 100 of the brain in the healthy state has a function capacity enough to be capable of simultaneously controlling the speaking motion and controlling the motion of the hands and feet. It is also supposed that some disease occurs in the brain and the capacity of the object definition eloquent area 100 falls. Unless the fall of the capacity of the object definition eloquent area 100 progresses to such a degree that at least one of the control of the speaking motion and the control of the motion of the hands and feet is interfered with, the disease that has occurred in the brain cannot be detected by the brain function evaluation using only the control of the speaking motion or only the control of the motion of the hands and feet. In the present invention apparatus, however, it is possible to measure the load concerning the control of the speaking motion for the capacity left in the object definition eloquent area 100 by, for example, controlling the generated load concerning the control of the motion of hands and feet and making it a bias for the object definition eloquent area 100.

In the apparatus according to the present invention, medical examination data concerning the health state of the brain can be obtained from living organism signals that can be easily measured, such as signals caused by the speaking voice, pulse wave, gravity center swinging and nystagmus. Therefore, the apparatus according to the present invention can be used in a preliminary diagnosis preceding close examination, which needs a large-scale device and a complicated diagnosis technique, and a medical examination in a medical checkup or the like.

Furthermore, the result of this evaluation and diagnosis can also be used for the investigation at the time of application for an insurance policy.

Furthermore, by combining the present invention apparatus with an apparatus such as the PET or SPECT, it is possible to monitor and control the load of the brain of the subject 20 in these apparatuses. The precision and reproducibility of a diagnosis using the PET or SPECT are implemented.

Owing to the present invention, it becomes possible to put the technique and apparatus capable of easily inspecting a brain disease to practical use. Instead of the conventional brain checkup, which cannot be widely executed because enormous time and expense are needed, the present invention apparatus makes possible implementation and spread of a brain dock of the next generation. The present invention has an extremely important significance in daily brain health management.

INDUSTRIAL APPLICABILITY

The present invention relates to a medical diagnosis technique for analyzing a time series signal, such as a voice, a pulse wave, swinging of gravity center, or nystagmus (ocular movement), emitted by a person, and thereby making a diagnosis to determine whether a disease is present in the brain of the person, and judge the progress situation and the state of the disease. By analyzing the living organism signals, such as the speaking voice, pulse wave, gravity center swinging and nystagmus, converted to digital data according to the chaos theoretical technique and calculating the chaos theoretical indexes, the activity state of the brain is sensed from the state of the chaos theoretical indexes. Therefore, examination data concerning the health state of the brain can be obtained from body signals that can be easily sampled. Therefore, the present invention can be used in a preliminary diagnosis preceding close examination, which needs a large-scale device and a complicated diagnosis technique, and a medical examination in a medical checkup or the like. Thus, the present invention is useful in the industry.

The invention claimed is:

1. A chaos theoretical brain function diagnosis apparatus for diagnosing a brain function of a subject by giving a load to a functional site of a living organism of the subject, receiving a reaction emitted from the living organism of the subject as an electric signal, and analyzing the electric signal, wherein the apparatus selects at least one from among a voice signal, a pulse wave signal and a gravity center swinging signal, in addition to a nystagmus signal, as the electric signal; calculates chaos theoretical indexes according to a chaos theoretical technique by using the selected signal and the nystagmus signal; detects changes in the chaos theoretical indexes with passage of time; and collectively evaluates and diagnoses the brain function.

2. The chaos theoretical brain function diagnosis apparatus according to claim 1, comprising:

a voice signal processor that divides the voice signal, which is input from a voice measuring instrument to the chaos theoretical brain function diagnosis apparatus and converted to a digital signal, into processing units, removes data other than speaking voice data of a human being, and extracts voice data of a single person, when the voice signal is voice data of a plurality of persons;

a chaos theoretical index calculator that analyzes speaking voice data of the single person, which is extracted in the voice signal processor, by using a chaos theoretical technique, calculates a chaos theoretical index, and stores a calculation result of the chaos theoretical index in an evaluation and diagnosis database; and a chaos theoretical index change state detector that detects a change state of the chaos theoretical index by comparing the calculation result of the chaos theoretical index with a chaos theoretical index of the voice signal of the same person at a different time point previously stored in the evaluation and diagnosis database.

3. The chaos theoretical brain function diagnosis apparatus according to claim 1, comprising:

a pulse wave signal processor that divides the pulse wave signal, which is input from a pulse wave measuring instrument to the chaos theoretical brain function diagnosis apparatus and converted to a digital signal, into processing units, and removes data other than pulse wave data;

a chaos theoretical index calculator that analyzes pulse wave data with data other than the pulse wave data removed in the pulse wave signal processor, by using a chaos theoretical technique, calculates a chaos theoretical index, and stores a calculation result of the chaos theoretical index in an evaluation and diagnosis database; and a chaos theoretical index change state detector that detects a change state of the chaos theoretical index by comparing the calculation result of the chaos theoretical index with a chaos theoretical index of the pulse wave signal of the same person at a different time point previously stored in the evaluation and diagnosis database.

4. The chaos theoretical brain function diagnosis apparatus according to claim 1, comprising:

a load generation section and a sensor section, wherein the load generation section comprises at least one of an image display device for imposing a visual load on the subject, a speaker for imposing an auditory load on the subject, and a sporting good having a function of swinging the gravity center, and wherein the sensor section comprises at least two measuring instruments of a microphone, a voice measuring instrument, a nystagmus instrument, a nystagmus measuring instrument, a pulse wave sensor, a pulse wave measuring instrument, a gravity center swinging instrument, and a swinging measuring instrument.

5. The chaos theoretical brain function diagnosis apparatus according to claim 4, further comprising:

a measuring instrument load controller that controls load state generated by the load generation section, and at least one of display contents displayed on an image display device, sound contents generated by the speaker, and motion contents generated in the sporting good is adjusted on the basis of at least one of a chaos theoretical index value of speaking voice data, a chaos theoretical index value of pulse wave data, and a chaos theoretical index value of gravity center swinging data, which are found by the chaos theoretical index calculator.

6. The chaos theoretical brain function diagnosis apparatus according to claim 1, wherein an evaluation and a diagnosis of the brain function are conducted by comparing data in a brain function evaluation and diagnosis database, which stores data for conducting an evaluation and a diagnosis of the brain function, with calculation results of the chaos theoretical indexes.

7. A chaos theoretical brain function diagnosis apparatus for diagnosing a brain function of a subject by giving a load to a functional site of a living organism of the subject, receiving a reaction emitted from the living organism of the subject as an electric signal, and analyzing the electric signal, wherein the apparatus selects at least two from among a voice signal, a nystagmus signal, a pulse wave signal and a gravity center swinging signal as the electric signal; calculates chaos theoretical indexes according to a chaos theoretical technique; detects changes in the chaos theoretical indexes with passage of time; and collectively evaluates and diagnoses the brain function, and wherein the chaos theoretical brain function diagnosis apparatus comprises:

a nystagmus signal processor that divides the nystagmus signal, which is input from a nystagmus measuring instrument to the chaos theoretical brain function diagnosis apparatus and converted into a digital signal, into processing units, and removes data other than nystagmus data;

a chaos theoretical index calculator that analyzes nystagmus data with data other than the nystagmus data removed in the nystagmus signal processor, by using a chaos theoretical technique, calculates a chaos theoretical index, and stores a calculation result of the chaos theoretical index in an evaluation and diagnosis database; and a chaos theoretical index change state detector that detects a change state of the chaos theoretical index by comparing the calculation result of the chaos theoretical index with a chaos theoretical index of the nystagmus signal of the same person at a different time point previously stored in the evaluation and diagnosis database.

8. A chaos theoretical brain function diagnosis apparatus for diagnosing a brain function of a subject by giving a load to a functional site of a living organism of the subject, receiving a reaction emitted from the living organism of the subject as an electric signal, and analyzing the electric signal, wherein the apparatus selects at least two from among a voice signal, a nystagmus signal, a pulse wave signal and a gravity center swinging signal as the electric signal; calculates chaos theoretical indexes according to a chaos theoretical technique; detects changes in the chaos theoretical indexes with passage of time; and collectively evaluates and diagnoses the brain function, and wherein the chaos theoretical brain function diagnosis apparatus comprises:

a gravity center swinging signal processor that divides the gravity center swinging signal, which is input from a swinging measuring instrument to the chaos theoretical brain function diagnosis apparatus and converted to a digital signal, into processing units, and removes data other than gravity center swinging data;

a chaos theoretical index calculator that analyzes gravity center swinging data with data other than the gravity center swinging data removed in the gravity center swinging signal processor, by using a chaos theoretical technique, calculates a chaos theoretical index, and stores a calculation result of the chaos theoretical index in an evaluation and diagnosis database; and a chaos theoretical index change state detector that detects a change state of the chaos theoretical index by comparing the calculation result of the chaos theoretical index with a chaos theoretical index of the gravity center swinging signal of the same person at a different time point previously stored in the evaluation and diagnosis database.

9. A chaos theoretical brain function diagnosis apparatus for diagnosing a brain function of a subject by giving a load to a functional site of a living organism of the subject, receiving a reaction emitted from the living organism of the subject as an electric signal, and analyzing the electric signal,
 wherein the apparatus selects at least one from among a voice signal, a nystagmus signal and a pulse wave signal, in addition to a gravity center swinging signal, as the electric signal; calculates chaos theoretical indexes according to a chaos theoretical technique by using the selected signal and the gravity center swinging signal; detects changes in the chaos theoretical indexes with passage of time; and collectively evaluates and diagnoses the brain function.

10. The chaos theoretical brain function diagnosis apparatus according to claim 9, comprising:
 a voice signal processor that divides the voice signal, which is input from a voice measuring instrument to the chaos theoretical brain function diagnosis apparatus and converted to a digital signal, into processing units, removes data other than speaking voice data of a human being, and extracts voice data of a single person, when the voice signal is voice data of a plurality of persons;
 a chaos theoretical index calculator that analyzes speaking voice data of the single person, which is extracted in the voice signal processor, by using a chaos theoretical technique, calculates a chaos theoretical index, and stores a calculation result of the chaos theoretical index in an evaluation and diagnosis database; and
 a chaos theoretical index change state detector that detects a change state of the chaos theoretical index by comparing the calculation result of the chaos theoretical index with a chaos theoretical index of the voice signal of the same person at a different time point previously stored in the evaluation and diagnosis database.

11. The chaos theoretical brain function diagnosis apparatus according to claim 9, comprising:
 a pulse wave signal processor that divides the pulse wave signal, which is input from a pulse wave measuring instrument to the chaos theoretical brain function diagnosis apparatus and converted to a digital signal, into processing units, and removes data other than pulse wave data;
 a chaos theoretical index calculator that analyzes pulse wave data with data other than the pulse wave data removed in the pulse wave signal processor, by using a chaos theoretical technique, calculates a chaos theoretical index, and stores a calculation result of the chaos theoretical index in an evaluation and diagnosis database; and
 a chaos theoretical index change state detector that detects a change state of the chaos theoretical index by comparing the calculation result of the chaos theoretical index with a chaos theoretical index of the pulse wave signal of the same person at a different time point previously stored in the evaluation and diagnosis database.

12. The chaos theoretical brain function diagnosis apparatus according to claim 9, comprising:
 a load generation section and a sensor section,
 wherein the load generation section comprises at least one of an image display device for imposing a visual load on the subject, a speaker for imposing an auditory load on the subject, and a sporting good having a function of swinging the gravity center, and
 wherein the sensor section comprises at least two measuring instruments of a microphone, a voice measuring instrument, a nystagmus instrument, a nystagmus measuring instrument, a pulse wave sensor, a pulse wave measuring instrument, a gravity center swinging instrument, and a swinging measuring instrument.

13. The chaos theoretical brain function diagnosis apparatus according to claim 9, wherein an evaluation and a diagnosis of the brain function are conducted by comparing data in a brain function evaluation and diagnosis database, which stores data for conducting an evaluation and a diagnosis of the brain function, with calculation results of the chaos theoretical indexes.

14. The chaos theoretical brain function diagnosis apparatus according to claim 12, further comprising:
 a measuring instrument load controller that controls a load state generated by the load generation section, and at least one of display contents displayed on an image display device, sound contents generated by the speaker, and motion contents generated in the sporting good is adjusted on the basis of at least one of a chaos theoretical index value of speaking voice data, a chaos theoretical index value of pulse wave data, and a chaos theoretical index value of gravity center swinging data, which are found by the chaos theoretical index calculator.

* * * * *